US006394993B1

(12) United States Patent
Chang et al.

(10) Patent No.: US 6,394,993 B1
(45) Date of Patent: May 28, 2002

(54) PROTECTIVE SPIKING PORT, CONTAINER IMPLEMENTING SAME AND METHOD FOR PROTECTING A CONTAINER

(75) Inventors: Shen-Youn Chang, Wadsworth; Tom Lillegard, Crystal Lake, both of IL (US); Paul Lin, Fullerton, CA (US); Lyman Aldrich, New Fairfield, CT (US)

(73) Assignee: Nestec, Ltd., Vevey (CH)

( * ) Notice: Subject to any disclaimer, the term of this patent is extended or adjusted under 35 U.S.C. 154(b) by 496 days.

(21) Appl. No.: 08/859,763

(22) Filed: May 21, 1997

(51) Int. Cl.$^{7}$ ................................................ A61B 19/00

(52) U.S. Cl. ................. 604/415; 383/202; 128/DIG. 24

(58) Field of Search ................................ 604/403, 408, 604/415, 905, 411; 128/DIG. 24; 206/828; 383/200, 202

(56) References Cited

U.S. PATENT DOCUMENTS

| | | | | | |
|---|---|---|---|---|---|
| 356,544 | A | | 1/1887 | Parker | |
| 2,698,619 | A | | 1/1955 | Beachem et al. | |
| 2,949,712 | A | | 8/1960 | Bieberdorp et al. | |
| 3,030,952 | A | | 4/1962 | Elder | |
| 3,177,870 | A | | 4/1965 | Salem, Jr. et al. | |
| 3,968,195 | A | | 7/1976 | Bishop | |
| 3,991,912 | A | | 11/1976 | Soto | |
| 4,078,699 | A | | 3/1978 | Hurtado | |
| 4,187,893 | A | | 2/1980 | Bujan | |
| 4,191,231 | A | | 3/1980 | Winchell et al. | |
| 4,202,334 | A | | 5/1980 | Elson | |
| 4,230,115 | A | | 10/1980 | Walz, Jr. et al. | |
| 4,305,443 | A | | 12/1981 | Bayham | |
| 4,441,538 | A | | 4/1984 | Larkin et al. | |
| 4,484,916 | A | | 11/1984 | McPhee | |
| 4,516,977 | A | | 5/1985 | Herbert | |
| 4,637,934 | A | | 1/1987 | White | |
| 4,723,956 | A | | 2/1988 | Schnell et al. | |
| 4,732,299 | A | | 3/1988 | Hoyt | |
| 4,946,040 | A | * | 8/1990 | Ipenburg | 383/202 |
| 5,125,919 | A | | 6/1992 | Miller et al. | |
| 5,334,180 | A | * | 8/1994 | Adolf et al. | 604/411 |
| 5,514,123 | A | * | 5/1996 | Adolf et al. | 604/411 |
| 5,674,209 | A | * | 10/1997 | Yarger | 604/905 |

FOREIGN PATENT DOCUMENTS

| | | | | | |
|---|---|---|---|---|---|
| DE | 4029521 | A1 | * | 3/1992 | 604/403 |
| DE | 42 34 957 | A1 | | 4/1994 | |
| EP | 1104359 | | | 7/1966 | |
| EP | 0 734 709 | A2 | | 3/1996 | |
| GB | 1358379 | | * | 7/1974 | 604/408 |

* cited by examiner

*Primary Examiner*—Dennis Ruhl
(74) *Attorney, Agent, or Firm*—Bell, Boyd & Lloyd LLC

(57) ABSTRACT

A protective port and container that incorporates the protective port are provided as well as a method for protecting a container. The protective port is attachable to the container by conventional methods and includes faces that are bendable from a base member that includes tubular ports extending therefrom. The faces protect the port from accidental penetration by a pierceable member and further provide a rigid gripping surface to manipulate the access openings to simplify the insertion of the pierceable member into one or both of the access openings.

18 Claims, 3 Drawing Sheets

PROTECTIVE SPIKING PORT, CONTAINER IMPLEMENTING SAME AND METHOD FOR PROTECTING A CONTAINER

BACKGROUND OF THE INVENTION

The present invention generally relates to a port, a container and a method for protecting a container. More specifically, the present invention relates to a protective, reinforcing port, a flexible container incorporating such a port and a method for protecting a container from, for example, accidental needle spiking or puncture.

It is, of course, generally known to provide fluids to a patient, either intravenously or enterally, as a method of treating a patient for various medical conditions or providing nutrition. Frequently, the fluids administered to a patient are contained in a flexible container.

One method of forming a flexible container is to seal two flexible sheets about the periphery of the sheets to create a cavity. A port is frequently placed between the sheets during the sealing process to create communication between the cavity and the exterior of the container to provide a means for introducing fluid into or dispensing fluid from the container.

A typical method, especially in the field of enteral nutrition feeding, for accessing the contents of a container provides for the use of a spike. The spike is used to access the container to allow the contents to drain through the spike. Such a container requires a spike accessing port of some kind to be sealed to the bag. As a result, during feeding, a spike is required to penetrate, for example, a pierceable film, which can be either part of the port or the container itself.

One issue with these types of containers' spike arrangements is that the containers may not be rigid enough to provide a firm gripping of the container during spiking. This can make it difficult to penetrate the container during the spiking. The access ports of the containers may also be difficult to stabilize and otherwise manipulate. Another issue that arises is that there is the problem of accidentally piercing of the container with the spike.

A need, therefore, exists for an improved protective port that may be simply incorporated with a container as well as a method for protecting a container.

SUMMARY OF THE INVENTION

A container and protective port are provided to assist in attaching a spike through an opening of the protective port into the container having a liquid or other product that requires draining for consumption, such as in the field of enteral nutrition feeding. Moreover, a method is provided for reinforcing a container as well as protecting the container from puncture.

To this end, in an embodiment of the present invention, a port is provided for attachment to a container. The port has a planar body having a first face and a second face. A first tubular port extends from the first face in a direction substantially perpendicular to the planar body wherein the planar body is constructed from a material that is bendable at opposite sides of the first tubular port at a point at which the first tubular port extends from the planar body wherein the second face of the planar body attaches to the container. An access opening extends through the first tubular port.

In an embodiment, a rib circumferentially surrounds the first tubular port.

In an embodiment, a second tubular port extends substantially parallel to the first tubular port and extends from the first face of the planar body with an access opening extending through the second tubular port.

In an embodiment, a reinforcing member extends between the first tubular port and the second tubular port and from the first face of the body.

In an embodiment, the planar body is bendable at opposite sides of the first tubular port and the second tubular port.

In an embodiment, the first tubular port has a substantially uniform circumference.

In an embodiment, the flaps of the planar body are bendable to extend from the planar body in a direction opposite to the first tubular port.

In an embodiment, the dimension of each flap between the first tubular port and a distal edge of the flap is longer than the length of the first tubular port.

In an embodiment, the tubular port and the planar body are integrally formed.

In another embodiment of the present invention, a port is provided for attachment to a container. The port has a planar body with a first face and a second face. A first tubular port extends from the first face in a direction substantially perpendicular to the planar body and is positioned such that the planar body forms a pair of flaps of substantially equal size and each extends from an opposite side of the first tubular port. The dimension of each flap between the first tubular port and a distal edge of the flap is longer that the length of the first tubular port. The planar body is bendable at opposite sides of the first tubular port such that the flaps may be bent out of the plane formed by the planar body. The second face of the planar body is attachable to the container and an access opening extends through the first tubular port.

In another embodiment of the present invention, a container is provided which is formed of at least one sheet of material and having a seal peripherally formed around edges of the sheet to form a cavity for housing a product. The container has a port attachable to one of the edges of the sheet having a thin body having a first face and a second face wherein the second face is attachable to the sheet. A first tubular port extends from the first face of the thin body having an access opening therethrough such that fluid communication can be provided from the cavity through the access opening of the first tubular port. The thin body is bent at opposite sides of the first tubular port forming a substantially U-shaped cross-section for attachment of the second face of the port to the sides of the sheet.

In an embodiment, a second tubular port extends from the first face of the thin body parallel to the first tubular port. The second tubular port has an access opening extending therethrough.

In an embodiment, the thin body and the first tubular port are integrally formed.

In an embodiment, a reinforcing member is integrally formed between the first tubular port and the second tubular port.

In another embodiment of the present invention, a method is provided for protecting a container. The method comprises the steps of: attaching a port to a container, the port having a thin, planar body having a first face and a second face with a first tubular port extending from the first face, the first tubular port having an access opening extending through the first tubular port; and bending the planar body at opposite sides of the first tubular port to surround opposite sides of the container wherein the opposite sides of the planar body are bent to form a substantially U-shaped cross-section for attachment of the second face of the port to the sides of the sheet.

In an embodiment, a second tubular port is provided extending parallel to the first tubular port.

In an embodiment, a connection between the first tubular port and the second tubular port is reinforced.

In an embodiment, the planar body and the first tubular port are integrally formed.

In an embodiment, the bent opposite faces of the planar body are secured to the container.

In an embodiment, ribs are provided peripherally around the first tubular port.

It is, therefore, an advantage of the present invention to provide a protective port and a container and a method for protecting a container that prevent needle spikes into the container.

Another advantage of the present invention is to provide a protective port, a container and a method for protecting a container that provide a gripping surface at the point that the port is attached to the container.

Yet another advantage of the present invention is to provide a protective port, a container and a method for protecting a container that provide a protective area at the point at which access is required to the container.

Another advantage of the present invention is to provide a protective port and a container that is simple in design.

Yet another advantage of the present invention is to provide a protective port, a container and a method for protecting a container that are economical to manufacture.

These and other advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides a container and a port attachable to the container through which access to an interior of the container is provided through the port. Moreover, the present invention provides a method for protecting a container from, for example, puncture as well as a reinforced gripping surface for the container.

Figure 1:
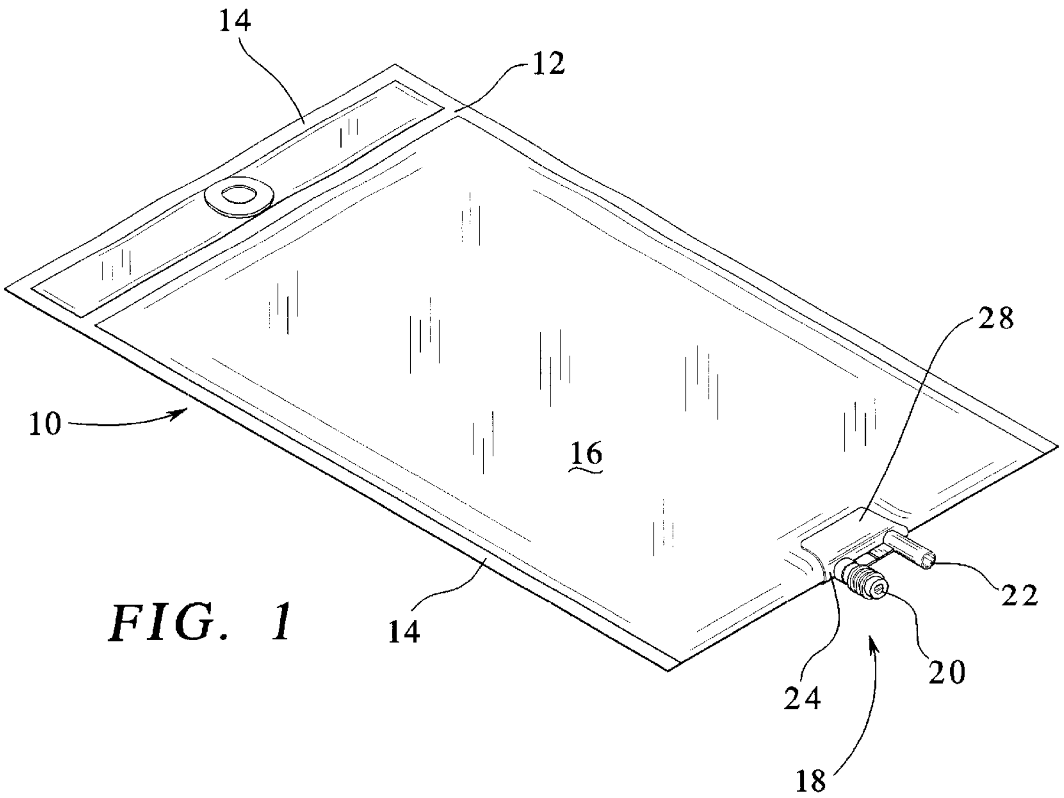
FIG. 1 illustrates a perspective view of an embodiment of a container with an embodiment of a protective port of the present invention.

Referring now to the drawings wherein like numerals represent like parts, FIG. 1 illustrates a flexible container 10 that is formed of at least one sheet of material 12. The container 10 is sealed about the edges 14 of the material 12 to form a cavity 16 within an interior of the container 10. A port 18 is located at the bottom of the container 10. The port 18, in the embodiment illustrated in FIG. 1, includes two access openings 20, 22. The port 18 further includes a base 24 having faces 26, 28 extending from the base 24.

Figure 2:
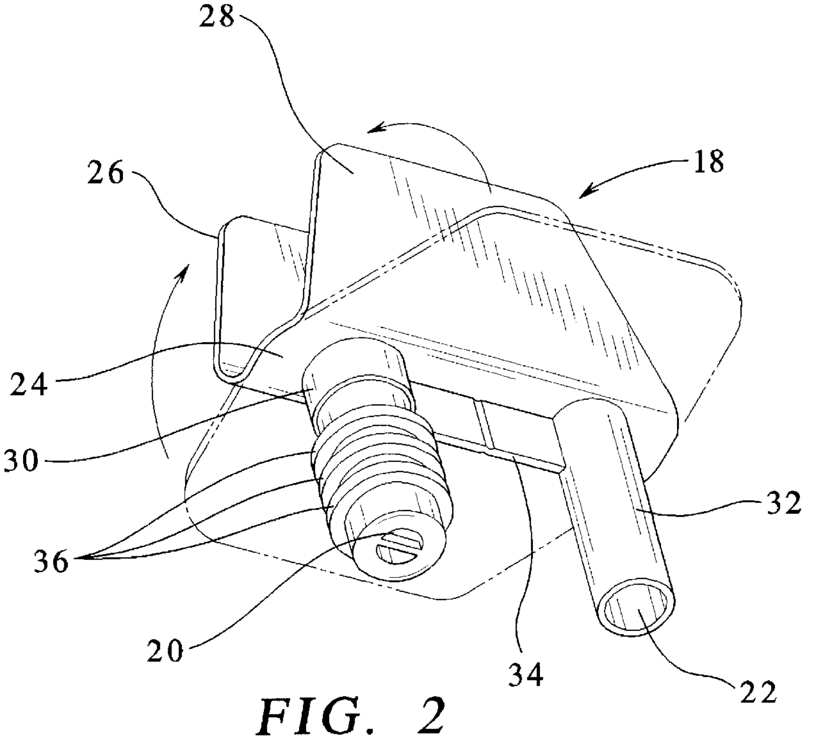
FIG. 2 illustrates a perspective view of an embodiment of a port of the present invention.

As illustrated in FIG. 2, the port 18 is constructed of a material that is rigid, yet bendable. The base 24 is integrally formed with the faces 26,28 such that the faces 26,28 may be bent in the position illustrated in FIG. 2. During bending of the faces 26,28, the base 24 remains substantially rigid with tubular ports 30,32 projecting substantially perpendicularly from the base 24 as illustrated. Between the tubular ports 30,32 is a reinforcing member 34 that reinforces the rigidity between the tubular ports 30,32. The access openings 20,22 extend through the tubular ports 30,32 into the base 24 of the port 18. Although two tubular ports 30,32 are illustrated, it should be understood that the port 18 could be constructed with a single tubular port or more than two tubular ports.

Figure 3:
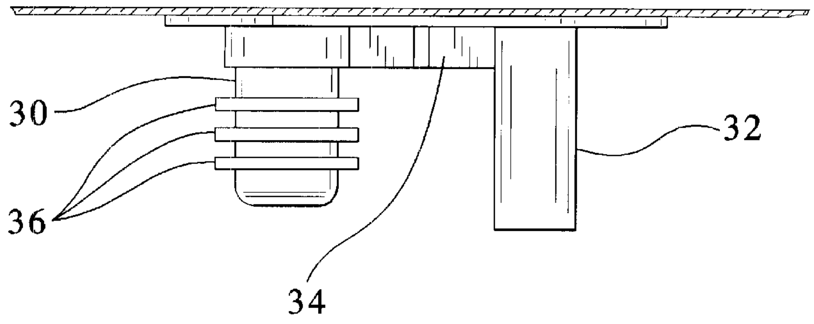
FIG. 3 illustrates a plan view of an embodiment of a port of the present invention.

In an embodiment, as illustrated in FIG. 3, one of the tubular ports 30 may include ribs 36 around a periphery of the tubular port. The ribs 36 assist in attachment of certain spikes or tubular members including spikes to the port 18. Of course, both of the tubular ports 30,32 may incorporate ribs around the periphery of the tubular ports 30,32.

Figure 4:
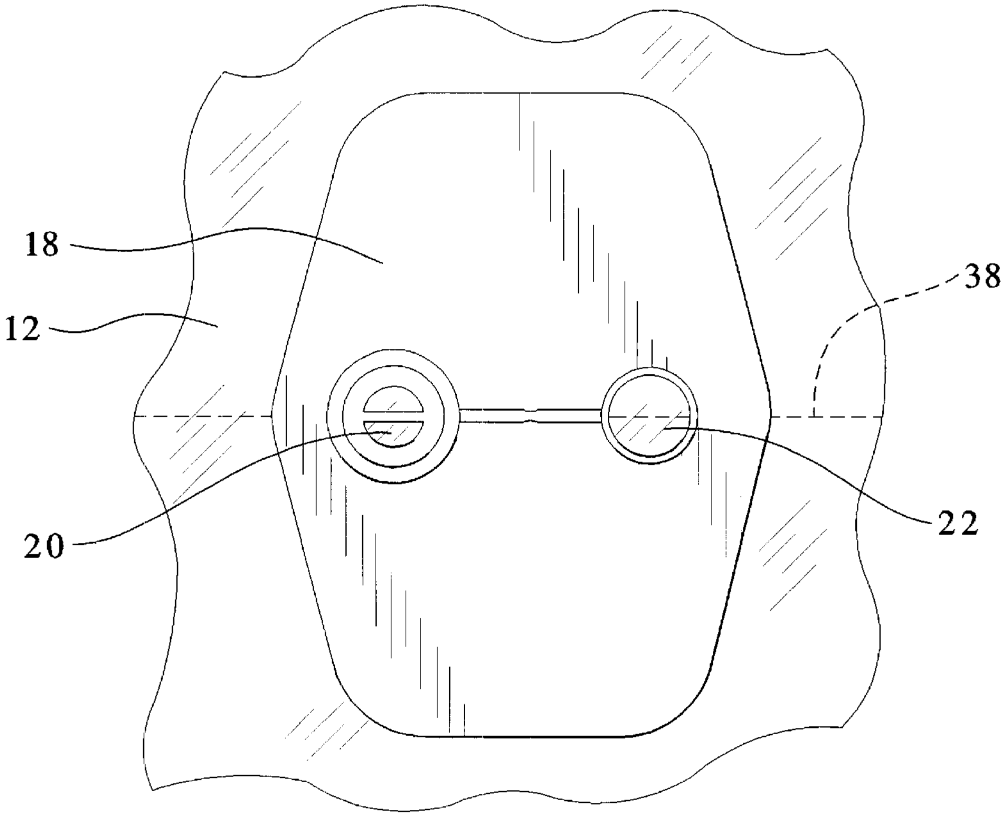
FIG. 4 illustrates a bottom view of an embodiment of a port of the present invention.

Referring now to FIG. 4, the port 18 is attachable to the flexible material 12 of the container 10. The port 18 may be mounted such that the access openings 20,22 are aligned along a center line 38. Conventional attaching techniques may be implemented by those skilled in the art and should not be deemed limiting to the present invention. The port 18 may be bent as illustrated in FIG. 2, either prior to or after attachment to the flexible material 12 of the container 10.

Within the access openings 20,22, a pierceable membrane (not shown) may be provided to provide access to the openings 20,22 and, ultimately, the interior cavity 16 of the container 10. Alternatively, only the material 12 of the container 10 may require piercing in order to obtain access to the interior cavity 16. Preferably, the interior cavity 16 includes a solution, such as an enteral nutrition product, that may be gravity fed from the interior cavity 16 of the container 10 through one of the access openings 20 or 22 through the tubular ports 30 or 32 of the port 18. Alternatively, one of the tubular ports 30,32 may serve as a feeding port to provide a mixing agent into the cavity 16 of the container 10 to mix with the solution therein. Alternatively, a solution may be added through one of the access openings 20,22 to mix with a product within the interior 16 of the container 10 that requires mixing before administration to, for example, a patient.

Figure 5:
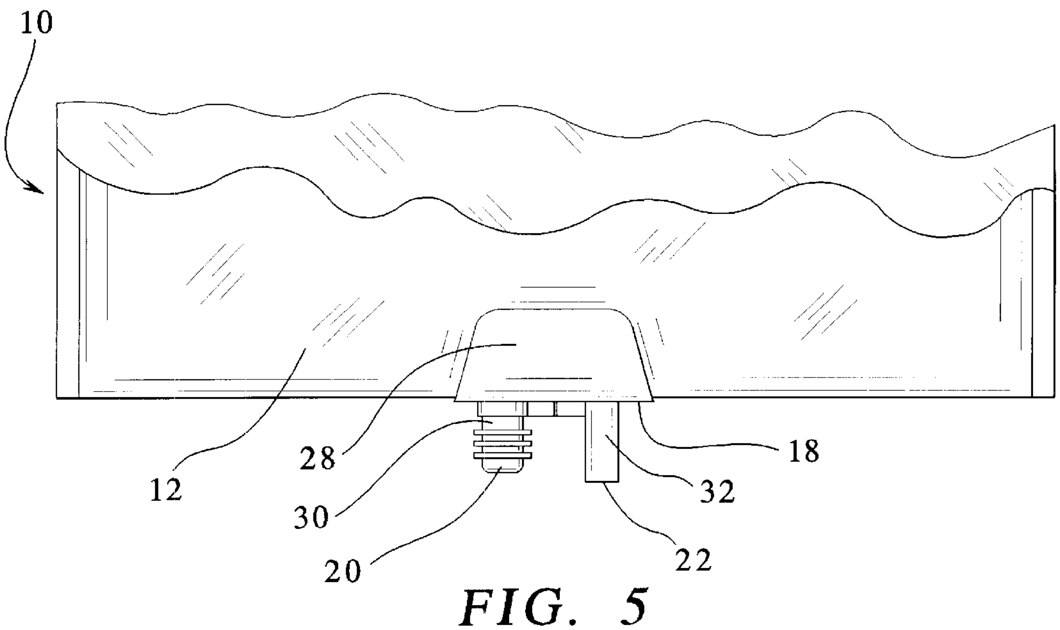
FIG. 5 illustrates a face view of an embodiment of a port attached to a container of the present invention.

As shown in FIG. 5, the port 18 is attached to the material 12 of the container 10 by conventional techniques, and the faces 26,28 are folded as illustrated. As a result, when the port 18 is used, a pierceable member, such as a needle, may be inserted through one or both of the access openings 20,22 of the tubular ports 30,32, respectively. The design of the port 18, particularly with the faces 26,28 and the base 24, provides a rigid construction that can be gripped by an individual and manipulated to align the pierceable member with one or both of the access openings 20,22. Further, the design of the port 18 prevents accidental piercing of the container 10 except through the access openings 20,22 that extend through the tubular ports 30,32, respectively.

Figure 6:
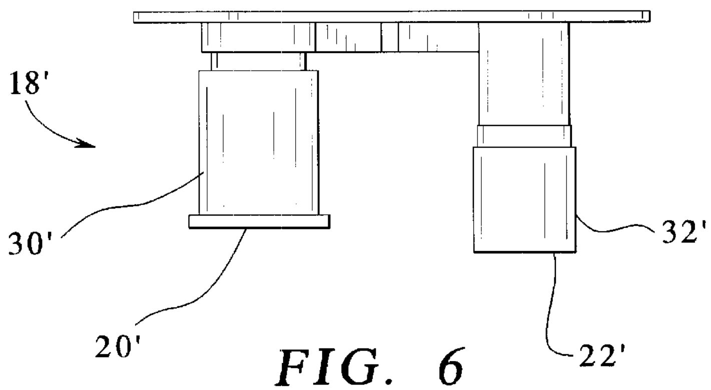
FIG. 6 illustrates a face view of another embodiment of a port of the present invention.

FIG. 6 illustrates an alternate embodiment of a port 18' of the present invention that incorporates tubular ports 30', 32' having access openings 20', 22', respectively, extending through the tubular ports 30', 32'. In the embodiment illustrated, the tubular ports 30', 32' do not include ribs and are designed to receive a pierceable member without a necessary friction fit between, for example, a tubular member, or connection member that necessitates the use of the ribs 36 as illustrated with reference to the embodiment shown and described in the previous figures. Of course, one skilled in the art could implement any type of tubular port that extends from a base of a port that embodies the principles described with reference to FIGS. 1–6 for the particular connecting mechanism that attaches to the tubular ports.

As previously set forth, the port 18 may be integrally formed including integral formation of the tubular ports 30,32. The port 18 is constructed of a rigid material that is easily attachable to the flexible material 12 by conventional methods. As previously set forth, although the port 18 is constructed of a material that is incapable of penetration by, for example, accidental needle spikes, the material of the port 18 must also be capable of bending as illustrated for attachment to the container 10.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

We claim:

1. A container formed of at least one sheet of material defining a cavity for housing a fluid product, the container having a port assembly attached to an edge of the container, the port assembly comprising:

a thin body having an outer face and an inner face attached to the container, the thin body being bent around the edge of the container for defining a pair of flaps, one on either side of the edge; and a first tubular port projecting from the outer face of the thin body and having a base end, a distal end and an access opening extending through it for providing fluid communication to the cavity, the base end being positioned between the flaps substantially in alignment with the edge of the container and spaced from any periphery of the thin body wherein the dimension of each flap between the edge of the container and a furthest distal edge of the flap is longer than the distance between the base end and distal end of the first tubular port.

2. The container of claim 1 in which a rib circumferentially surrounds the first tubular port.

3. The container of claim 1 further comprising:

a second tubular port extending from the outer face of the thin body at a position between the flaps substantially in alignment with the edge of the container and substantially parallel to the first tubular port, the second tubular port having an access opening extending through it.

4. The port of claim 3 further comprising:

a reinforcing member extending between the first tubular port and the second tubular port and from the first face of the body.

5. The container of claim 1 wherein the first tubular port has a substantially uniform circumference.

6. The container of claim 1 wherein the first tubular port and the thin body are integrally formed.

7. A container formed of at least one sheet of material defining a cavity for housing a fluid product, the container having a port assembly attached to an edge of the container, the port assembly comprising:

a thin body having an outer face and an inner face attached to the container, the thin body being bent around the edge of the container for defining a pair of substantially identical flaps, one on either side of the edge; and a first tubular port projecting from the outer face of the thin body and having a base end, a distal end and an access opening extending through it for providing fluid communication to the cavity, the base end being positioned between the flaps substantially in alignment with the edge of the container and spaced from any periphery of the thin body wherein the dimension of each flap between the edge of the container and a furthest distal edge of the flap is longer than the distance between the base end and distal end of the first tubular port.

8. A container formed of at least one sheet of material and having a seal peripherally formed around edges of the sheet to form a cavity for housing a product, the container comprising:

a port attached to one of the edges of the sheet, the port having a thin body having a first face and a second face, the second face being attached to the sheet and further wherein a first tubular port and a second tubular port each extend from the first face of the thin body and each have an access opening therethrough such that fluid communication can be provided from the cavity through the access opening of either tubular port, the thin body being bent at opposite sides of the tubular ports forming a substantially U-shaped cross-section for attachment of the second face of the port to sides of the sheet wherein a distance from a distal end of the thin body to a side of the first tubular port is greater than a length of the first tubular port.

9. The container of claim 8 wherein the thin body and the first tubular port are integrally formed.

10. The container of claim 8 further comprising:

a reinforcing member integrally formed between the first tubular port and the second tubular port.

11. The container of claim 8 wherein the thin body extends a distance up sides of the container greater than the length of the first tubular port.

12. A method for protecting a container, the method comprising the steps of:

attaching a port to a container, the port having a thin, planar body having a first face and a second face with a first tubular port extending from the first face, the first tubular port having an access opening extending through the first tubular port; and bending the planar body at opposite sides of the first tubular port to surround opposite sides of the container wherein the opposite sides of the planar body are bent to form a substantially U-shaped cross-section for attachment of the second face of the port to the sides of the sheet.

13. The method of claim 12 further comprising the step of:

providing a second tubular port extending parallel to the first tubular port.

14. The method of claim 13 further comprising the step of:

reinforcing a connection between the first tubular port and the second tubular port.

15. The method of claim 12 wherein the planar body and the first tubular port are integrally formed.

16. The method of claim 12 further comprising the step of:

securing the bent opposite faces of the planar body to the container.

17. The method of claim 12 further comprising the step of:

providing ribs peripherally around the first tubular port.

18. The method of claim 12 wherein the thin body extends a distance up sides of the container greater than the length of the tubular port.

* * * * *